US009040094B2

(12) United States Patent
Ono et al.

(10) Patent No.: US 9,040,094 B2

(45) Date of Patent: May 26, 2015

(54) FLAKY PARTICLE AND COSMETIC

(71) Applicant: Sakai Chemical Industry Co., Ltd., Sakai-shi, Osaka (JP)

(72) Inventors: Keiji Ono, Iwaki (JP); Takuro Ashida, Iwaki (JP); Hiroyuki Izumikawa, Iwaki (JP); Hirobumi Yoshida, Iwaki (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 14/511,925

(22) Filed: Oct. 10, 2014

(65) Prior Publication Data

US 2015/0030768 A1 Jan. 29, 2015

Related U.S. Application Data

(62) Division of application No. 12/449,413, filed as application No. PCT/JP2007/052523 on Feb. 13, 2007, now abandoned.

(51) Int. Cl.

| | |
|---|---|
| ***A61K 8/02*** | (2006.01) |
| ***A61K 8/25*** | (2006.01) |
| ***A61K 8/26*** | (2006.01) |
| ***A61Q 1/02*** | (2006.01) |
| ***C09C 1/28*** | (2006.01) |
| ***C09C 3/08*** | (2006.01) |
| ***A61Q 19/00*** | (2006.01) |
| ***A61K 8/23*** | (2006.01) |
| ***A61K 8/36*** | (2006.01) |
| ***B05D 1/18*** | (2006.01) |

(52) U.S. Cl.

CPC .............. *A61K 8/0258* (2013.01); *A61Q 19/00* (2013.01); *A61K 8/25* (2013.01); *A61K 8/23* (2013.01); *A61K 8/26* (2013.01); *A61K 8/361* (2013.01); *B05D 1/18* (2013.01); *A61K 2800/805* (2013.01); *A61K 2800/622* (2013.01); *A61K 2800/30* (2013.01)

(58) Field of Classification Search

CPC ..... A61K 2800/412; A61K 8/02; A61K 8/19; A61K 8/25; A61K 8/26; A61Q 1/02; C01P 2004/20; C01P 2004/54; C01P 2004/61; C09C 1/027; C09C 1/28; C09C 1/405; C09C 1/407; C09C 3/08

See application file for complete search history.

(56) References Cited

U.S. PATENT DOCUMENTS

| | | | | |
|---|---|---|---|---|
| 3,656,982 A | | 4/1972 | Chapman et al. | |
| 4,098,878 A | | 7/1978 | Baines et al. | |
| 4,648,908 A | * | 3/1987 | Takasuka et al. | 106/417 |
| 4,710,375 A | | 12/1987 | Takasuka et al. | |
| 5,171,572 A | | 12/1992 | Suganuma et al. | |
| 5,262,148 A | | 11/1993 | Sugasawa et al. | |
| 5,340,582 A | | 8/1994 | Sugasawa et al. | |
| 6,432,535 B1 | | 8/2002 | Noguchi et al. | |
| 6,511,536 B1 | | 1/2003 | Noguchi et al. | |
| 6,652,844 B1 | | 11/2003 | Arseguel et al. | |
| 2001/0007677 A1 | | 7/2001 | Nagatani et al. | |
| 2004/0126320 A1 | | 7/2004 | Miyamoto et al. | |
| 2006/0079422 A1 | | 4/2006 | Midha et al. | |
| 2006/0225617 A1 | | 10/2006 | Ismail et al. | |
| 2007/0020208 A1 | | 1/2007 | Gutkowski et al. | |
| 2009/0060960 A1 | | 3/2009 | Biehl et al. | |

FOREIGN PATENT DOCUMENTS

| | | |
|---|---|---|
| EP | 0445785 | 9/1991 |
| EP | 1 712 596 | 10/2006 |
| JP | 60-69011 | 4/1985 |
| JP | 61-100508 | 5/1986 |
| JP | 62-49247 | 10/1987 |
| JP | 3-257016 | 11/1991 |
| JP | 4-108716 | 4/1992 |
| JP | 7-291623 | 11/1995 |
| JP | 2001-98186 | 4/2001 |
| JP | 2001-199826 | 7/2001 |
| JP | 2002-080748 | 3/2002 |
| JP | 2002-265218 | 9/2002 |
| JP | 2003-40736 | 2/2003 |
| JP | 2004-300080 | 10/2004 |
| WO | WO-2007/009887 | 1/2007 |

OTHER PUBLICATIONS

Singer et al. (Fundamentals of Friction 1992, Springer, pp. 11, 239, and 268.

Mica; [online] retrieved on Jul. 28, 2011 from: http://en.wikipedia.org/wiki/Mica; 8 pages.

Talc; [online] retrieved on Jul. 28, 2011 from: http://en.wikipedia.org/wiki/Talc; 5 pages.

Aluminum oxide; [online] retrieved on Jul. 28, 2011 from: http://en.wikipedia.org/wiki/Aluminum_oxide; 6 pages.

* cited by examiner

*Primary Examiner* — Ernst V Arnold

(74) *Attorney, Agent, or Firm* — Jordan and Hamburg LLP

(57) ABSTRACT

The present invention has an object to provide a flaky particulate material giving skin an excellent smoothness, which is free from whitening problem upon use thereof owing to its high transparency. The present invention also has another object to provide a cosmetic composition containing the flaky particulate material. The present invention relates to flaky particulate material, which has an average coefficient of friction is not more than 0.50, and a total light transmittance is not less than 85%. A particle in the flaky particulate material comprises a substrate particle made of one material selected from the group consisting of mica, a synthetic mica, sericite, talc, barium sulfate and aluminum oxide. The present invention provides a flaky particulate material that gives skin excellent smoothness, a natural tone, and a matt appearance. The flaky particulate material of the present invention gives a cosmetic composition which provides great comfort of use, and an excellent appearance.

4 Claims, No Drawings

FLAKY PARTICLE AND COSMETIC

STATEMENT OF RELATED APPLICATIONS

The present application is a divisional application of co-pending U.S. application Ser. No. 12/449,413 filed Nov. 3, 2009; which is the U.S. national stage of International Application No. PCT/JP2007/052523, filed on Feb. 13, 2007. The disclosures of these applications are incorporated herein by reference.

BACKGROUND OF THE INVENTION

The present, invention relates to a flaky particulate material and a cosmetic composition.

Flaky particles are excellent in adhesion to skin, and also excellent in smoothness owing to their shapes. Thus, such flaky particles can provide great comfort of use, and therefore, are widely used in makeup cosmetics.

A variety of flaky particulate materials are known as such flaky particles. Among them, particulate materials with a small coefficient of friction provides excellent smoothness, and thus, a cosmetic composition that provides great comfort of use can be obtained from such flaky particulate materials. A flaky particulate material with a particularly small coefficient of friction is, for example, boron nitride, which is mentioned in Patent Document 1.

Boron nitride has indeed good smoothness, but it is somewhat whitish. Thus, the boron nitride has a defect that it looks whitish, on skin upon use. For giving skin a natural tone, it is difficult to increase a formulation amount of boron nitride in cosmetic compositions. On the other hand, other flaky particulate materials such as talc, mica, sericite, barium sulfate, or aluminum oxide, are inferior to boron nitride in smoothness, although they are superior in transparency. That is, no flaky particulate material suitable for a cosmetic composition providing high transparency, and sufficient smoothness comparable to boron nitride, has been known yet in the art.

Patent Document 2 discloses a surface-treatment of boron nitride particles with a fatty acid metal salt for improving comfort of use, adhesion, and persistence of make up, of the particles. However, such a surface-treatment is unsuccessful to improve transparency of boron nitride particles, and thus, cannot produce a flaky particulate material with both sufficient transparency and smoothness. An alternative treatment, which includes a surface-treatment of a pigment for a cosmetic composition with a fatty acid metal salt, have been also known (See Patent Document 3, for example), but the treatment is intended for enhancing dispersibility of the pigment, or providing adhesion or water repellency to the pigment. Thus, no report specialized in an improvement of smoothness has been found yet in the art.

[Patent Document 1] Japanese Kohyo (Examined) Publication S62-49247

[Patent Document 2] Japanese Kokai (Unexamined) Publication 2003-40736

[Patent Document 3] Japanese Kokai (Unexamined) Publication S60-69011

SUMMARY OF THE INVENTION

In view of the state of the art, the present invention has an object to provide a flaky particulate material which provides excellent smoothness and high ability to give skin a natural tone, and is free from a whitening problem upon use thereof.

The present invention also has another object to provide a cosmetic composition containing this flaky particulate material.

On aspect of the present invention relates to a flaky particulate material, which has an average coefficient of friction of not more than 0.50, and a total light transmittance of not less than 85%.

Preferably, a particle in the flaky particulate material contains a base particle made of at least one material selected from the group consisting of mica, a synthetic mica, sericite, talc, barium sulfate and aluminum oxide.

The particle of the flaky particulate material may preferably contain 0.1 to 15 mass % of a fatty acid metal salt that is deposited on the substrate particle by surface treatment.

The flaky particulate material preferably has a reflection-intensity ratio (0°/45°) of not less than 0.30. The ratio (0°/45°) means a ratio: (a reflection intensity in the condition that the light incident angle is −45° and an acceptance angle is 0°)/(a reflection intensity in the condition that the light incident angle is −45° and the acceptance angle is 45°), and the ratio is measurable by a three-dimensional variable gloss meter.

Another aspect of the present invention relate to a cosmetic composition that contains at least one species of the above flaky particulate materials.

Hereafter, the present invention will be described in detail.

The flaky particulate material of the present invention is excellent in smoothness and transparency, and thus can provide great comfort of use and excellent cosmetic, finish once it is blended in a cosmetic composition. That is, owing to high smoothness and transparency, the flaky particulate material of the present invention can simultaneously+ give skin a natural tone, natural cosmetic finish, and great comfort of use, which have never been attained yet by conventional flaky particulate materials.

The flaky particulate material of the present invention is preferably one having a high reflection-intensity ratio (0°/45°). A pigment with a high reflection-intensity ratio (0°/45°) gives skin a matt appearance, and a cosmetic composition containing such a pigment can attain matt finish. In this respect, characteristics of the flaky particulate material of the present, invention is different from that of boron nitride, which is highly glossy and can not give skin a matt appearance. For a cosmetic composition, nonglossy and matt finish is often required. Thus, pigments that give skin a matt appearance are highly desired.

The flaky particulate material of the present invention has average coefficient of friction of 0.50 or less. In the description for the present invention, an "average coefficient of friction" means an average of coefficients of friction in 20 mm length, measured by Friction Tester KES-SE (a product of Kato Tech. Co., Ltd) with a silicone rubber friction block. The larger an average coefficient of friction of a sample is, the poorer the smoothness of the sample is. The average coefficient of friction of over 0.50 leads to a problem of poor smoothness. The average coefficient, of friction is preferably 0.45 or less.

The flaky particulate material of the present invention has transparency such as total light transmittance of 85% or higher. Here, a testing sample for the total light transmittance may be produced by kneading the flaky particulate material with liquid paraffin SMOIL™ P-80 (a product of Matsumura Oil Research Corp.) in a Hoover's muller, to prepare a 20 mass %-concentration paste, and then forming a 25-μm thin film from the paste using an applicator. A cosmetic composition containing the flaky particulate material of the present invention with total light transmittance of not lower than 85% is free from whitening problem on shin upon use. In the description for the present invention, total light transmittance may be measured by a haze meter HM-150 (a product of Murakami Color Research Laboratory, Co., Ltd.) in accordance with JIS K 7361. The total light transmittance is preferably 86.5% or higher.

The flaky particulate material of the present invention preferably has a reflection-intensity ratio (0°/45°) of not less than 0.30. Here, the reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), and the ratio is measurable by a three-dimensional variable gloss meter.

That, is, the flaky particulate material of the present invention is preferably a material with the above ratio, which gives skin a low-glossy, matt appearance, usually, the reflection-intensity ratio (0°/45°) of particles of less than 0.30 means that the particles are shiny. Shiny particle have smooth, particulate surfaces, and smoothness thereof is intrinsically excellent. On the other hand, when the reflection-intensity ratio (0°/45°) of particles is not less than 0.30, reflection intensity (scattering reflection intensity) is high, and the particle with such an intensity ratio looks matt. Such particles have essentially poor smoothness because of surface roughness. However, a particle in the flaky particulate material of the present invention has a treated surface, which may be treated as mentioned above, and therefore, is preferable in that the material has both a matt appearance and excellent smoothness. Thus, a cosmetic composition containing the flaky particulate material gives skin a matt appearance, as well as good smoothness. The reflection intensity at an acceptance angle of 0°, and the reflection intensity at an acceptance single of 45° may be measured as a reflection intensity to light which is incident at an angle of −45°, by extending a test sample over a material, such as a synthetic leather, with a cosmetic powder-puff to uniformly orientate the ingredients in the test sample, and measured by Three-dimensional auto-goniophotometer GP-200 (a product of Murakami Color Research Laboratory, Co., Ltd.)

Furthermore, it is preferable that a particle in the flaky particulate material has an average length of the major axis of 3 to 40 μm, and the ratio: (average length of the major axis)/(average particle thickness) of 3 to 300. If the average length of the major axis is less than 3 μm, a cosmetic composition containing such a flaky particulate material may cause frictional feeling when applied on skin and may nave poor smoothness. If the length of the average major axis exceeds 40 μm, a cosmetic composition containing the flaky particulate material may be granular in touch when applied on skin and may have poor smoothness.

If the ratio: (average length of the major axis)/(average particle thickness) is less than 3, a cosmetic, composition containing such a flaky particulate material may cause frictional feeling when applied on skin and may have poor smoothness. If the ratio: (average length of the major axis)/(average particle thickness) exceeds 300, a cosmetic composition, containing arch a flaky particulate material may be granular in touch when applied on skin, and may have poor smoothness.

The average length of the major axis means an average of the maximum diameters of 30 particles on a line that is drawn at random in a scanning electron micrograph of powdery flakes. The average particle thickness means an average value of the thickness of 30 particles, which is determined in a similar way.

It is preferable that a particle in the flaky particulate material contains a substrate made of one material selected from the group consisting of mica, synthetic mica, sericite, talc, barium sulfate, and aluminum oxide. A substrate particle mentioned above is excellent in transparency, and therefore, the flaky particulate material having the above certain range of the light transmittance can be obtained.

On the contrary, boron nitride or the like hardly provides clear particles even with surface-treatment, although boron nitride is excellent in surface smoothness. Thus, it is unsuitable to use to achieve the purpose of the present invention.

A preferable flaky particulate material of the present invention may be obtained by surface-treating a substrate particle, which is made of one species selected from the group consisting of the above mica, synthetic mica, sericite, talc, barium sulfate and aluminum oxide. The preferable resultant flaky particulate material has a reduced average coefficient of friction. An untreated mica, synthetic mica, sericite, talc, barium sulfate or aluminum oxide pigment has excellent transparency, but does not have such a high smoothness as boron nitride. Therefore, the pigment may be appropriately surface-treated, to produce a flaky particulate material with the above properties. Treated particles have excellent smoothness and transparency. Thus, a makeup cosmetic composition containing such treated particles provides great comfort of use and natural finish.

In addition, many of materials that provide a matt appearance contain particles with poor surface smoothness or have a broad particle distribution, and as a result, smoothness tends to be poor. A flaky particulate material with the above properties may be produced by appropriately surface-treating such materials. Thus-treated particulate material has excellent smoothness, transparency, and gives skin a matt appearance. Thus, the treated particulate material can provide great comfort of use and natural matte finish.

The at least one species, which are to be used as the substrate particles, selected from the group consisting of mica, synthetic mica, sericite, talc, barium sulfate and aluminum oxide is not particularly limited, and any material of a cosmetically available grade may be used. Examples of commercially-available one include synthetic mica PDM-10S (a product, of Topy industries Ltd.), sericite FSE (a product of Sanshin Mining Ind. Co., Ltd.), sericite SL (a product of Horie Kako, K.K.), talc Micro Ace P-2 (a product, of Nippon talc Co., Ltd.), lamellar barium sulfate.H (a product of Sakai Chemical Industry Co., Ltd.)

The above-mentioned surface treatments are not particularly limited, and a treatment with a fatty acid metal salt is preferable. The fatty acid metal salt is not particularly limited, and one having an alkyl moiety that contains more carbon atoms is preferable, and especially, one having an alkyl moiety that contains 12 or more carbon atoms is more preferable, in view of pleasant feeling after application on skin, and excellent storage stability as a cosmetic composition containing the flaky particulate material. The fatty-acid moiety in the above fatty acid metal salt may derived from any of saturated fatty acids such as lauric acid, myristic acid, palmitic acid, and stearic acid; unsaturated fatty acids such as oleic acid; branched fatty acids such as isostearic acid. The aliphatic-acid moiety also may derived from any of naturally-occurring fatty acids such as a coconut oil fatty acid, tallowate, a palm oil fatty acid, palm kernel oil, and papas oil. The above fatty acids may be used singly or in combination of two or more of them. More preferable are laurates, palmitates, and stearates, and the most preferable are palmitates and stearates. The metal in the fatty acid metal salt is not particularly limited, and preferable examples of fatty acid metal salts include salts of a bivalent or trivalent metal. Specific examples include calcium salts, magnesium salts, zinc salts, and aluminum salts. Among them, calcium salts, magnesium salts, and aluminum salts are preferable.

The treatment with a fatty acid metal salt is not particularly limited. One non-limiting example is a method including depositing a coating layer of a fatty acid metal salt on the surface of substrate particles by suspending the above substrate particles in water to prepare slurry, then adding to the slurry an aqueous solution of a water-soluble metal salt and an aqueous basic solution to basify the slurry, and adding dropwise an aqueous solution of a water-soluble fatty acid salt to the slurry.

Specifically, the treatment may be carried out in the following manner:

(1) Substrate particles are suspended in water, then a water-soluble magnesium salt such as magnesium chloride, magnesium sulfate, magnesium nitrate or magnesium acetate, or a water-soluble calcium salt such as calcium chloride, calcium nitrate or calcium acetate, is added in such an appropriate amount that the amount of aliphatic metal salts on a treated flaky particulate material should be 0.1 to 15% by mass, and then an alkali is added to the resultant slurry over 30 minutes or more, to basify the slurry to be within the pH range of 10 to 11.

(2) The slurry is heated to a temperature of 50° C. to 80° C., and then an aqueous solution of a fatty acid salt such as sodium, potassium, or ammonium salt is added dropwise thereto over 30 minutes or more in such an amount that the amount of aliphatic metal salts on a treated flaky particulate material should be 0.1 to 15% by mass, and the slurry is aged over 30 minutes or more.

(3) After aging, the pH of the slurry is adjusted to be 7 to 8 with an acid, and then the slurry was filtered. The filtered solid matter was washed and then dried.

It is preferable to treat the above substrate particles with a fatty acid metal salt in such an amount that the amount of aliphatic metal salts on a treated flaky particulate material should be 0.1 to 15% by mass of the flaky particulate material as a treated product basis. If the amount is less than 0.1% by mass, improvement of smoothness may be insufficient, whereas the proportion exceeds 15% by mass, smoothness may be poor.

The present invention relates to a cosmetic composition containing one or two or more species of the flaky particulate materials as mentioned above. The cosmetic composition of the present invention is particularly preferably a makeup cosmetic composition, and specific examples thereof include base makeup cosmetic compositions such as foundations, face powders, and makeup bases; point makeup cosmetic compositions such as lipsticks, eye shadows, and cheek colors. The cosmetic composition of the present invention preferably contains 1 to 50% by mass of the flaky particulate material.

A cosmetic composition of the present invention may comprise, in addition to line above flaky particulate material, another flaky particle whose average coefficient of friction and total light transmittance are out of the above range, or a variety of color pigment or extenders with different shapes.

The cosmetic composition, of the present invention may be used together with any color pigments, extenders, aqueous components, and oily components.

The color pigment is not particularly limited, and examples thereof include inorganic white pigments (for example, titanium dioxide, zinc oxide, etc.); inorganic red pigments (for example, iron oxide (colcothar), iron titanate, etc.); inorganic brown pigments (for example, γ-iron oxide, etc.); inorganic yellow pigment (for example, yellow iron oxide, ocher, etc.); inorganic black pigments (for example, black iron oxide, lower-order titanium oxide, etc.); inorganic purple pigments for example, mango violet, cobalt violet, etc.): inorganic green pigments (for example, chromium oxide, chromium hydroxide, cobalt titanate, etc.); inorganic blue or blue-like pigments (for example, ultramarine, iron blue, etc.); pearl pigment (for example, titanium oxide-coated mica, titanium oxide-coated bismuth oxychloride, titanium oxide-coated talc, color titanium oxide-coated mica, bismuth oxychloride, bismuth oxychloride, argentine, etc.); metallic powder pigments (for example, aluminum powder, copper powder, etc.); organic pigments such as zirconium, barium or aluminum lake (for example, organic pigments such as red No. 201, red No. 202, red No. 204, red No. 205, red No. 220, red No. 226, red No. 228, red No. 405, orange No. 203, orange No. 204, yellow No. 205, yellow No. 401, and blue No. 404; red No. 3; red No. 104; red No. 106; red No. 227; red No. 210; red No. 401; red No. 505; orange No. 205; yellow No. 4; yellow No. 5; yellow No. 202; yellow No. 203; green No. 3; and blue No. 1, etc.); and natural pigments (for example, chlorophyll, β-carotene, etc.). The above extender is not particularly limited and examples thereof include mica, synthetic mica, sericite, talc, kaolin, calcium carbonate, magnesium carbonate, barium sulfate, and aluminum oxide.

The above aqueous components and oily components are not particularly limited, and the cosmetic composition of the present invention may contain an oil, a surfactant, a moisturizer, a higher alcohol, a sequestering agent, a natural or synthetic polymer, a water-soluble or oil-soluble polymer, a UV absorber, one or more of a variety of extracts, an inorganic or organic pigment, an inorganic or organic clay mineral, an inorganic or organic pigment which is treated with a silicone, a colorant such as an organic dye, a preservative, an antioxidant, a coloring matter, a thickener, a pH adjuster, a perfume, a cooling agent, an antiperspirant, an antiseptic, or a skin activating agent. Specifically, a desired cosmetic composition may be prepared by blending any one, or two or more of the components mentioned below in a conventional, manner. The blending amounts of these components are not particularly limited as long as the effects of the present invention are not impaired.

The oil is not particularly limited, and examples thereof include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed, oil, perilla oil, soybean oil, arachis oil, tea seed oil, kaya oil, rice bran oil, Chinese tung oil, Japanese tung oil, jojoba oil, germ oil, triglycerol, glyceryl trioctanoate, glyceryl tripalmitate, cacao butter, coconut oil, horse fat, hydrogenated coconut oil, palm oil, beef tallow, mutton tallow, hydrogenated beef tallow, palm kernel oil, lard, beef bone tallow, Japanese tallow-kernel oil, a hydrogenated oil, neatsfoot oil, Japanese tallow, hydrogenated castor oil, yellow beeswax, candelilla wax, cotton wax, carnauba wax, barberry wax, insect wax, spermaceti wax, montan wax, bran wax, lanolin, kapok wax, lanolin acetate, liquid lanolin, sugarcane wax, isopropyl lanolate, hexyl laurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, vaseline, and microcrystalline wax.

The lipophilic nonionic surfactant is not particularly limited, and example thereof include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerol fatty acid esters such as monoglycerides of fatty acids of cottonseed oil, glyceryl monoerucate, glyceryl sesquioleate, glyceryl monostearate, α,α'-glyceryl oleate pyroglutamate, and glyceryl (stearate/malate); glycerol aliphatic acid esters such as propylene glycol monostearate; hydrogenated castor oil derivatives; and glycerol alkyl ethers.

The hydrophilic nonionic surfactant is not particularly limited and examples thereof include POE sorbitan fatty acid esters such as POE sorbitan monooleate, POE-sorbitan monostearate, POE-sorbitan monooleate, and POE-sorbitan tetra oleate; POE sorbitol fatty acid esters such as POE-sorbitol monolaurate, POE-sorbitol monooleate, POE-sorbitol pentaoleate, and POE-sorbitol monostearate; POE-glycerol fatty acid esters such as POE-glycerol monostearate, POE-glycerol monoisostearate, and POE-glycerol triisostearate; POE fatty acid esters such as POE monooleate, POE distearate, POE monodioleate, and ethylene glycol distearate; POP alkyl ethers each as POE lauryl ether, POE oleyl ether, POE stearyl ether, POE behenyl ether, POE 2-octyldodecyl ether, and POE cholestanol ether; POE alkyl phenyl ethers such as POE octylphenyl ether, POE nonylphenyl ether, and POE dinonylphenyl ether; pluaronics such as pluronic; POE-POP alkyl ethers such as POE-POP cetyl ether, POE-POP 2-decyl tetradecyl ether, POE-POP monobutyl ether; POE-POP hydrogenated lanolin, and POE-POP glycerol ether, tetra POE-tetra POP ethylenediamine condensates such as Tetronic™; POE castor oil- or hydrogenated castor oil-derivatives such as POE castor oil, POE hydrogenated castor oil, POE hydrogenated castor oil monoisostearate, POE hydrogenated castor oil triisostearate, monopyroglutamic acid monoisostearic acid diester and POE hydrogenated castor oil maleic acid; POP beeswax-lanolin derivatives, such as POE sorbitol beeswax; alkanol amides such as coconut oil-fatty acid diethanol amides, lauric acid monoethanol amide, and fatty acid isopropanol amide; POE propylene glycol fatty acid esters; POE alkylamines; POE fatty acid amides; sucrose fatty acid esters, POE nonylphenyl formaldehyde condensates; alkyl ethoxydimethylamine oxides; and trioleyl phosphate.

Examples of other surfactants which may be blended in the cosmetic composition include anionic surfactants such as fatty acid soaps, higher-alkyl sulfuric-acid ester salts, triethanolamine POE lauryl sulfate, and alkyl ether sulfuric ester salts; cationic surfactants such as alkyl trimethylammonium salts, alkyl pyridinium salts, alkyl quaternary ammonium salts, alkyl dimethyl benzyl ammonium salts, POE alkyl amines, alkyl amine salts, and polyamine fatty acid derivatives; and amphoteric surfactants such as imidazoline amphoteric surfactants, and betain surfactants. These surfactants may be blended in an amount such that the stability of the cosmetic composition is maintained, and problematic skin irritation is not caused.

The moisturizer is not particularly limited, and examples thereof include xylitol, sorbitol, maltitol, chondroitin sulfuric acid, hyaluronic acid, mucoitin sulfuric acid, caronic acid, atelocollagen, cholesteryl 12-hydroxystearate, sodium lactate, bile salts, dl-pyrrolidone carboxylates, short chain soluble collagens, diglycerol (EO) PO adducts, Rosa roxburghii extract, Yarrow (Achillea milefolium) extract, and melilot extract.

The higher alcohol is not particularly limited, and examples thereof include linear alcohols such as lauryl alcohol cetyl alcohol, stearyl alcohol, behenyl alcohol, myristyl alcohol, oleyl alcohol, and cetostearyl alcohol; and branched alcohols such as monostearyl glycerol ether (batyl alcohol), 2-decyltetradecynol, lanolin alcohol, cholesterol, phytosterol, hexyldodecanol, isostearyl alcohol, and octyldodecanol.

The sequestering agent is not particularly limited, and examples thereof include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

A natural water-soluble polymer is not particularly limited, and examples thereof include vegetable-derived polymers such as gum arabic, tragacanth gum, galactan, guar gum, carob gum, karaya gum, carrageenan, pectin, agar, quince seed (quince), algaecolloid (algae extract), and starch (rice, corn, potato, and wheat); microorganism-derived polymers such as xanthan gum, dextran, succinoglucan, and pullulan; animal-derived polymers such as collagen, casein, albumin, and gelatin.

A half-synthesized water-soluble polymer is not particularly limited, and examples thereof include starch polymers such as carboxymethyl starch and methyl hydroxypropyl starch; cellulose polymers such as methyl cellulose, nitrocellulose nitrate, ethyl cellulose, methyl hydroxypropyl cellulose, hydroxyethyl cellulose, cellulose sodium sulfate, hydroxypropyl cellulose, carboxymethyl cellulose sodium (CMC), crystalline cellulose, and cellulose powder; sodium alginate, or alginate polymers such as propylene glycol alginate.

A synthetic water-soluble polymer is not particularly limited, and examples thereof include polyvinyl alcohol, polyvinyl methyl ether, and polyvinyl, pyrrolidone; polyoxyethylene polymers such as polyethylene glycol 20,000, 40,000, and 60,000 grades; copolymers such as polyoxyethylene polyoxypropylene copolymer; acrylic polymers such as sodium polyacrylate, polyethylacrylate, and polyacrylamide; polyethyleneimine; and cationic polymers.

A water-soluble inorganic polymer is not particularly limited, and examples thereof include bentonite, magnesium aluminum silicate (veegum), laponite, hectorite, and silicic anhydride.

The UV absorber is not particularly limited, and examples thereof include benzoate UV absorbers such as p-aminobenzoic acid (hereafter abbreviated to PABA), PABA monoglycerol ester, N,N-dipropoxy PABA ethyl ester, N,N-diethoxy PABA ethyl ester, N,N-dimethyl PABA ethyl ester, and N,N-dimethyl PABA butyl ester; anthranilate UV absorbers such as homomenthyl-N-acetyl anthranilate; salicylate UV absorbers such as amyl salicylate, menthyl salicylate, homomentyl salicylate, octyl salicylate, phenyl salicylate, benzyl salicylate, and p-isopropanol phenyl salicylate; cinnamate UV absorbers such as octyl cinnamate, ethyl 4-isopropyl cinnamate, methyl 2,5-diisopropyl cinnamate, ethyl 2,4-diisopropyl cinnamate, methyl 2,4-diisopropyl cinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glycerylmono-2-ethylhexanoyl diparamethoxycinnamate; benzophenone UV absorbers such as 2,4-dihydroxy benzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'- phenyl-benzophenone-2-carboxylate, 2-hydroxy-4-n-octoxybenzophenone, and 4-hydroxy-3-carboxybenzophenone; 3-(4'-methylbenzyliene)-d,l-camphor; 3-benzylidene-d,l-camphor; urocanic acid; urocanic acid ethyl ester; 2-phenyl-5-methylbenzoxazole; 2,2'-hydroxy-5-methylphenyl benzotriazol; 2-(2'-hydroxy-5'-t-octylphenyl)benzotriazol; 2-(2'-hydroxy-5'-methylphenyl)benzotriazol; dibenzalazine; dianisoyl methane; 4-methoxy-4'-t-butyldibenzoylmethane; and 5-(3,3-dimethyl-2-norbornylidene)-3-pentane-2-one.

Examples of such a variety of extracts include saururaceous extract, Phellodendron bark extract, dead nettle extract, glycyrrhiza extract, peony root extract, bouncing Bet extract, luffa extract, cinchona extract, strawberry geranium extract, sophorae radix extract, nupharextract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, bachelor button extract, hamamelis extract, placenta extract, thymic extract, silk extract, and licorice extract, although the examples are not limited thereto.

The other components which may be blended are not particularly limited, and examples thereof include vitamins such as vitamin A oil, retinal, retinol palmitate, inositol, pyridoxine hydrochloride, benzyl nicotinate, nicotinamide, dl-α-tocopherol nicotinate, magnesium ascorbyl phosphate, 2-O-α-D-glucopyranosyl L-ascorbic acid, vitamin D2 (ergocalciferol), DL-α-tocopherol, DL-α-tocopherol acetate, pantothenic acid, and biotin; hormones such as estradiol, and ethynyl estradiol; amino acids such as arginine, aspartic acid, cystine, cysteine, methionine, serine, leucine, and tryptophan; anti-inflammatory agents such as allantoin, azulene, and glycyrrhizic acid; whitening agents such as arbutin; astringents such as tannic acid; inorganic pigments such as carbon black; fatty acids such as lauric acid, myristic acid, palmitic acid, stearic acid, oleic acid, and isostearic acid, as well as addition salts of the fatty acids, such as sodium salts, potassium salts, calcium salts, magnesium salts, strontium salts, and barium salts; refrigerants such as L-menthol and camphor; sulfur; lysozyme chloride; pyridoxine chloride; and silicone oil.

The flaky particulate material of the present invention contains, as a main ingredient, a flaky particulate material with an average coefficient of friction of not more than 0.50, and a total light transmittance of not less than 85%, and it has excellent smoothness and transparency. Thus, a cosmetic composition containing such a flaky particulate material can provide great comfort of use and au excellent finish appearance. Furthermore, the flaky particulate material further satisfying the ratio (0°/45°) of not less than 0.30 gives a cosmetic composition which can provide a matt appearance. Thus, the flaky particulate material of the present invention provides a cosmetic composition, with greater comfort of use and a more excellent finish appearance than ever before.

The present invention provides a flaky particulate material that has excellent smoothness and transparency, and can provide a matt appearance. The flaky particulate material of the present invention gives a cosmetic composition which can provides great, comfort of use and an excellent appearance.

DETAILED DESCRIPTION OF THE INVENTION

Production of a Flaky Particulate Material

Example 1

In 2 liters of ion-exchanged water, 100 g of lamellar barium sulfate.H (average coefficient of friction: 0.61; a product, of Sakai Chemical Industry Co., Ltd) was suspended to prepare a suspension. A solution of 7.1 g of magnesium chloride hexahydrate in 50 mL of ion-exchanged water was added to the suspension, and then a 1-mass % aqueous NaOH solution was added over 30 minutes so that the pH of the mixture should be within 10 to 11. The mixture was heated to 70° C., and then a solution of 5.3 g of coconut oil fatty acid potassium salt in 50 mL of ion-exchanged water was added over 30 minutes. After completion of addition, the mixture was aged for 30 minutes, and adjusted the pH of the mixture to be within 7 to 8 with a 1-mass % aqueous sulfuric acid solution. The mixture was filtered. The solid matter filtered was washed with water (until the conductivity of washed liquid be 0.1 mS/cm or lower), and then dried, to give a flaky particulate material. Thus-obtained flaky particulate material had an average length of the major axis of 7.3 μm, the ratio of (average length of the major axis)/(average particle thickness) of 8.3, an average coefficient of friction of 0.42, a total light transmittance of 89.8, and a reflection-intensity ratio (0°/45°) of 0.37. The reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), which, was measured by a three-dimensional variable gloss meter.

Example 2

In 2 liters of ion-exchanged water, 100 g of lamellar barium sulfate.H (average coefficient of friction: 0.61) was suspended to prepare a suspension. A solution of 4.9 g of calcium chloride dihydrate in 50 mL of ion-exchanged, water was added to the suspension, and then a 1-mass % aqueous NaOH solution was added over 30 minutes so that the pH of the mixture should be within 10 to 11. The mixture was heated to 70° C., and then a solution of 5.9 g of potassium myristate in 50 mL of ion-exchanged water was added over 30 minutes. After completion of addition, the mixture was aged for 30 minutes, and adjusted the pH of the mixture to be within 7 to 8 with a 1-mass % aqueous sulfuric acid solution. The mixture was filtered. The solid matter filtered was washed with water (until the conductivity of washed liquid be 0.1 mS/cm or lower), and then dried, to give a flaky particulate material. Thus-obtained flaky particulate material had an average length of the major axis of 7.0 μm, the ratio of (average length of the major axis)/(average particle thickness) of 7.7, an average coefficient of friction of 0.44, a total light transmittance of 89.7, and a reflection-intensity ratio (0°/45°) of 0.37. The reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), which was measured by a three-dimensional variable gloss meter.

Example 3

In 2 liters of ion-exchanged water, 100 g of lamellar barium sulfate.H (average coefficient of friction: 0.61) was suspended to prepare a suspension. A solution of 3.3 g of calcium chloride dihydrate in 50 mL of ion-exchanged water was added to the suspension, and then a 1-mass % aqueous NaOH solution was added over 30 minutes so that the pH of the mixture should be within 10 to 11. The mixture was heated to 70° C., and then a solution of 4.4 g of potassium palmitate in 50 mL of ion-exchanged water was added over 30 minutes. After completion of addition, the mixture was aged for 30 minutes, and adjusted the pH of the mixture to be within 7 to 8 with a 1-mass % aqueous sulfuric acid solution. The mixture was filtered. The solid matter filtered was washed with water (until the conductivity of washed liquid be 0.1 mS/cm or lower), and then dried, to give a flaky particulate material. Thus-obtained flaky particulate material had an average length of the major axis of 7.7 μm, the ratio of (average length of the major axis)/(average particle thickness) of 8.0, average coefficient of friction of 0.45, total light transmittance of 89.5, and a ratio (0°/45°) of 0.37. The ratio (0°/45°) means the ratio of an intensity of reflection to light incident at −45° at an acceptance angle of 0° relative to that at an acceptance angle of 45°, as measured by a three-dimensional variable gloss meter.

Example 4

In 2 liters of ion-exchanged water, 100 g of sericite FSE (average coefficient of friction: 0.77; a product of Sanshin Mining Ind., Co., Ltd) was suspended to prepare a suspension. A solution of 7.0 g of magnesium, chloride hexahydrate in 50 mL of ion-exchanged water was added to the suspension, and then a 1-mass % aqueous NaOH solution was added over 30 minutes so that the pH of the mixture should be within 10 to 11. The mixture was heated to 70° C., and then a solution of 7.0 g of sodium stearate in 50 mL of ion-exchanged water was added over 30 minutes. After completion of addition, the mixture was aged for 30 minutes, and adjusted the pH of the mixture to be within 7 to 8 with a 1-mass % aqueous sulfuric acid, solution. The mixture was filtered. The solid matter filtered was washed with water (until the conductivity of washed liquid bit 0.1 mS/cm or lower), and then dried, to give a flaky particulate material. Thus-obtained flaky particulate material had an average length of the major axis of 14.7 μm, the ratio of (average length of the major axis)/(average particle thickness) of 47, an average coefficient of friction of 0.48, a total light transmittance of 87.8, and a reflection-intensity ratio (0°/45°) of 0.35. The reflection-intensity ratio (0°/45°) means the ratio of an intensity of reflection to light incident at −45° at an acceptance angle of 0° relative to that at an acceptance angle of 45°, as measured by a three-dimensional variable gloss meter.

Comparative Example 1

In 2 liters of ion-exchanged water, 100 g of lamellar barium sulfate.H (average coefficient of friction; 0.61) was suspended to prepare a suspension. A solution of 7.1 g of magnesium chloride hexahydrate in 50 mL of ion-exchanged water was added to the suspension, and then a 1-mass % aqueous NaOH solution was added over 5 minutes so that, the pH of the mixture should be within 10 to 11. The mixture was heated to 70° C., and then a solution of 5.8 g of coconut oil fatty acid potassium salt in 50 mL of ion-exchanged water was added over 30 minutes. After completion of addition, the mixture was aged for 30 minutes, and adjusted the pH of the mixture to be within 7 to 8 with a 1-mass % aqueous sulfuric acid solution. The mixture was filtered. The solid matter filtered was washed with water (until the conductivity of washed liquid be 0.1 mS/cm or lower), and then dried, to give a flaky particulate material. Thus-obtained flaky particulate material had an average length of the major axis of 7.0 μm, the ratio of (average length of the major axis)/(average particle thickness) of 8.1, an average coefficient of friction of 0.56, a total light transmittance of 89.5, and a reflection-intensity ratio (0°/45°) of 0.40. The reflection-intensity ratio (0°/45°) means the ratio of an intensity of reflection to light incident at −45° at an acceptance angle of 0° relative to that at an acceptance angle of 45°, as measured by a three-dimensional variable gloss meter.

Comparative Example 2

In 2 liters of ion-exchanged water, 100 g of lamellar barium sulfate.H (average coefficient of friction: 0.61; a product of Sakai Chemical Industry, Co., Ltd) was suspended to prepare a suspension. A solution of 7.1 g of magnesium chloride hexahydrate in 50 mL of ion-exchanged water was added to the suspension, and then a 1-mass % aqueous NaOH solution was added over 30 minutes so that the pH of the mixture should be within 10 to 11. The mixture was heated to 70° C., and then a solution of 5.8 g of coconut oil fatty acid potassium salt in 50 mL of ion-exchanged water was added over 5 minutes. After completion of addition, the mixture was aged for 30 minutes, and adjusted the pH of the mixture to be within 7 to 8 with a 1-mass % aqueous sulfuric acid solution. The mixture was filtered. The solid matter filtered was washed with water (until the conductivity of washed liquid be 0.1 mS/cm or lower), and then dried, to give a flaky particulate material. Thus-obtained flaky particulate material had an average length of the major axis of 7.3 μm, the ratio of (average length of the major axis)/(average particle thickness; of 8.6, an average coefficient of friction of 0.55, a total light transmittance of 89.8, and a reflection-intensity ratio (0°/45°) of 0.39. The reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), which was measured by a three-dimensional variable gloss meter.

Comparative Example 3

In 2 liters of ion-exchanged water, 100 g of lamellar barium sulfate.H (average coefficient of friction: 0.61; a product of Sakai Chemical Industry Co., Ltd.) was suspended to prepare a suspension. A solution of 7.1 g of magnesium chloride hexahydrate in 50 mL of ion-exchanged water was added to the suspension. The mixture was heated to 70° C., and then a solution of 5.8 g of coconut oil fatty acid potassium salt in 50 mL of ion-exchanged water was added over 30 minutes. After completion of addition, the mixture was aged for 30 minutes, and the mixture was filtered. The solid matter filtered was washed with water (until the conductivity of washed liquid be 0.1 mS/cm or lower, and then dried, to give a flaky particulate material. Thus-obtained, flaky particulate material had an average length of the major axis of 7.2 μm, the ratio of (average length of the major axis)/(average particle thickness) of 8.5, an average coefficient of friction of 0.54, a total light transmittance of 89.8, and a reflection-intensity ratio (0°/45°) of 0.38. The reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), which was measured by a three-dimensional variable gloss meter.

Comparative Example 4

In 2 liters of ion-exchanged water, 100 g of lamellar barium sulfate.H (average coefficient of friction: 0.61) was suspended to prepare a suspension. A solution of 0.04 g of calcium chloride dihydrate in 50 mL of ion-exchanged water was added to the suspension, and then a 0.3-mass % aqueous NaOH solution was added over 30 minutes so that the pH of the mixture should be within 10 to 11. The mixture was heated to 70° C., and then a solution of 0.05 g of potassium palmitate in 50 mL of ion-exchanged water was added over 30 minutes. After completion of addition, the mixture was aged for 30 minutes, and adjusted the pH of the mixture to be within 7 to 8 with a 0.3-mass % aqueous sulfuric acid solution. The mixture was filtered. The solid matter filtered was washed with water (until the conductivity of washed liquid be 0.1 mS/cm or lower), and then dried, to give a flaky particulate material. Thus-obtained flaky particulate material had an average length of the major axis of 7.9 μm, the ratio of (average length of the major axis)/(average particle thickness) of 8.4, an average coefficient of friction of 0.59, a total light transmittance of 89.8, and a reflection-intensity ratio (0°/45°) of 0.39. The reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), which was measured by a three-dimensional variable gloss meter.

Comparative Example 5

In 2 liters of ion-exchanged water, 100 g of sericite FSE (average coefficient of friction: 0.77) was suspended to prepare a suspension. A solution of 25.4 g of magnesium chloride hexahydrate in 50 mL of ion-exchanged water was added to the suspension, and then a 3-mass % aqueous NaOH solution was added over 30 minutes so that the pH of the mixture should be within 10 to 11. The mixture was heated to 70° C., and then a solution of 24.3 g of sodium stearate in 50 mL of ion-exchanged water was added over 30 minutes. After completion of addition, the mixture was aged for 30 minutes, and adjusted the pH to be within 7 to 8 with a 1-mass % aqueous sulfuric acid solution. The mixture was filtered. The solid matter filtered was washed with water (until the conductivity of washed liquid be 0.1 mS/cm or lower), and then dried, to give a flaky particulate material. Thus-obtained flaky particulate material had an average length of the major axis of 15.3 μm, the ratio of (average length of the major axis)/(average particle thickness) of 51, an average coefficient of friction of 0.72, a total light transmittance of 87.4, and a reflection-intensity ratio (0°/45°) of 0.38. The reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), which was measured by a three-dimensional variable gloss meter.

Referential Example 1

A product of boron nitride, "CREAM BLANCH" (a product of Mizushima Ferroalloy Co., Ltd) was analyzed. The analysis revealed that the "CREAM BLANCH" had an average length of the major axis of 9.5 μm, the ratio (average length of the major axis)/(average particle thickness) of 46, an average coefficient of friction of 0.50, a total light transmittance of 75.9, and a reflection-intensity ratio (0°/45°) of 0.24. The reflection-intensity ratio (0°/45°) means a ratio: (a reflection intensity in the condition that the light incident angle is −45° and an acceptance angle is 0°)/(a reflection intensity in the condition that the light incident angle is −45° and the acceptance angle is 45°), which was measured by a three-dimensional variable gloss meter.

The average coefficient of friction, the total light transmittance, and the reflection-intensity ratio (0°/45°) of the obtained flaky particulate material were measured in the following manner.

Calculation of an Average Coefficient of Friction

A 25-mm-width piece of a double stick tape was taped on a slide glass, and then a flaky particulate material was placed on the tape. The flaky particulate material was spread on the plate glass with a cosmetic powder-puff. The coefficient of friction of the sample was measured by Friction Tester KES-SE (a product, of Kato Tech Co., Ltd.) with a silicone rubber friction block. The average coefficients of friction were determined from, a 20-mm average of coefficient of friction (μ).

The average coefficient of friction of lamellar barium sulfate.H (particle size: 5 to 10 μm, a product of Sakai Chemical Industry Co., Ltd), which was used as a substrate particle, was 0.56.

Measurement of a Total Light Transmittance

A 2-g portion of a flaky particulate material and an 8-g portion of liquid paraffin SMOIL™ P-80 (a product of Matsumura Oil Research Corp.) were kneaded in a Hoover's muller, and then formed a 25-μm thin film from the resultant paste using an applicator. Total light transmittance of the thin film was measured with a haze meter HM-150 (a product of Murakami Color Research Laboratory, Co., Ltd.).

Measurement of a Reflection-Intensity Ratio (0°/45°)

A sample was placed on "SAPURERE" (protein powder-incorporated polyurethane-coated synthetic leather; a product of Idemitsu Technofine Co., Ltd.), and the sample was spread uniformly with a cosmetic sponge. The intensity of reflection of the sample to light that was incident at −45° was measured by a three-dimensional variable gloss meter GF-200 (a product of Murakami Color Research Laboratory, Co., Ltd.) The ratio of intensities of reflection: (the intensity at an acceptance angle of 0)/(the intensity at an acceptance angle of 45°) was calculated. The higher the above ratio is, the greater the degree of matte is.

As is to be understood from the results, sericite FSE and lamellar barium sulfate.H gives a greater matt appearance than boron nitride.

Amounts of fatty acid metal salts deposited on the obtained flaky particulate material are illustrated, in Table 1.

TABLE 1

| | Charged amount of a water-soluble salt (g) | Charged amount of a water-soluble fatty acid metal salt (g) | Deposited amount of the fatty acid metal salt (mass % of a flaky particulate material) |
|---|---|---|---|
| Example 1 | 7.1 | 5.8 | 5.7 |
| Example 2 | 4.9 | 5.9 | 6.0 |
| Example 3 | 3.3 | 4.4 | 4.5 |
| Example 4 | 7.0 | 7.0 | 6.8 |
| Compar. Ex 1 | 7.1 | 5.8 | 5.7 |

TABLE 1-continued

| | Charged amount of a water-soluble salt (g) | Charged amount of a water-soluble fatty acid metal salt (g) | Deposited amount of the fatty acid metal salt (mass % of a flaky particulate material) |
|---|---|---|---|
| Compar. Ex 2 | 7.1 | 5.8 | 5.7 |
| Compar. Ex 3 | 7.1 | 5.8 | 5.7 |
| Compar. Ex 4 | 0.04 | 0.05 | 0.05 |
| Compar. Ex 5 | 25.4 | 24.3 | 21.0 |

Production of a Cosmetic Composition

According to the formulas illustrated in the below Table 2, the components (1) to (7) were mixed, and the obtained mass was triturated. The triturated matter was transferred in a high-speed blender. The components (8) to (10) were mixed at 80° C. to dissolve them, and then the resultant solution was added to the high-speed blender. The mixture in the high-speed blended was uniformly mixed. The amounts of each component in Table 2 are expressed as mass %. The components (11) was further added to the mixture in the blender, and then mixed. Thus-obtained solid matter was triturated again, and then subjected to screening. The screened matter was compression-molded on a metal plate, to produce cosmetic compositions (Examples 5 to 8, Comparative examples 6 to 10, and Referential examples 2).

Evaluation of Cosmetic Compositions

Fifteen subjects evaluated the smoothness, the degree of a matt appearance on skin, and the degree of naturalness of a tone on skin, of each obtained cosmetic compositions after applied on skin. The results are illustrated in the below Table 2. The evaluation criteria is as follows:

S: Excellent

A: Good

B: Average

C: Bad

TABLE 2

| | Example | | | | Comparative Example | | | | | Ref. Ex. |
|---|---|---|---|---|---|---|---|---|---|---|
| | 5 | 6 | 7 | 8 | 6 | 7 | 8 | 9 | 10 | 2 |
| (1) Mica (as received: Y-3000: a product of Yamaguchi Mica Co., Ltd) | 6.5 | 6.5 | 6.5 | 6.5 | 6.5 | 6.5 | 6.5 | 6.5 | 6.5 | 6.5 |
| (2)※Flake particles | 50 (Ex. 1) | 50 (Ex. 2) | 50 (Ex. 3) | 50 (Ex. 4) | 50 (Compar. Ex. 1) | 50 (Compar. Ex. 2) | 50 (Compar. Ex. 3) | 50 (Compar. Ex. 4) | 50 (Compar. Ex. 5) | 50 (Ref. Ex. 1) |
| (3) Talc (as received: Micro Ace P-2: a product of Nippon Talc Co., Ltd) | 20 | 20 | 20 | 20 | 20 | 20 | 20 | 20 | 20 | 20 |
| (4) Titanium oxide | 10 | 10 | 10 | 10 | 10 | 10 | 10 | 10 | 10 | 10 |
| (5) Colcothar | 0.8 | 0.8 | 0.8 | 0.8 | 0.8 | 0.8 | 0.8 | 0.8 | 0.8 | 0.8 |
| (6) Yellow iron oxide | 2.5 | 2.5 | 2.5 | 2.5 | 2.5 | 2.5 | 2.5 | 2.5 | 2.5 | 2.5 |
| (7) Black iron oxide | 0.1 | 0.1 | 0.1 | 0.1 | 0.1 | 0.1 | 0.1 | 0.1 | 0.1 | 0.1 |
| (8) Liquid paraffin | 8 | 8 | 8 | 8 | 8 | 8 | 8 | 8 | 8 | 8 |
| (9) Yellow beeswax | 2 | 2 | 2 | 2 | 2 | 2 | 2 | 2 | 2 | 2 |
| (10) Preservative | Moderate amount | Moderate amount | Moderate amount | Moderate amount | Moderate amount | Moderate amount | Moderate amount | Moderate amount | Moderate amount | Moderate amount |
| (11) Perfume | Slight amount | Slight amount | Slight amount | Slight amount | Slight amount | Slight amount | Slight amount | Slight amount | Slight amount | Slight amount |
| Smoothness | S | S | S | S | B | B | B | B | C | S |
| Matted appearance | S | S | S | S | S | S | S | S | S | C |
| Transparency | S | S | S | S | S | S | S | S | S | C |

As illustrated in Table 2, it was found from the results in Table 2 that cosmetic compositions that gave skin excellent smoothness, a matt appearance and an excellent natural tone were obtained.

The present invention provides a flaky particulate material that gives a skin excellent smoothness, an excellent natural tone, and a matt appearance. The flaky particulate material of the present invention gives a cosmetic composition which provides a great comfort of use and an excellent appearance.

The invention claimed is:

1. A process for producing a flaky particulate material comprising substrate particles having surfaces coated with a fatty acid metal salt, the process comprising the steps of:

suspending the substrate particles in water, whereby a slurry is formed;

adding an aqueous solution of a water-soluble metal salt to the slurry in an amount sufficient to provide a fatty acid metal salt on the substrate particles in an amount of 0.1 to 15% by mass of the flaky particulate material;

adding an aqueous basic solution over a period of 30 minutes or more to basify the slurry;

adding an aqueous solution of a water-soluble fatty acid salt drop-wise to the slurry for 30 minutes or more in an amount sufficient to provide a fatty acid metal salt on the substrate particles in an amount of 0.1 to 15% by mass of the flaky particulate material; and ageing the slurry for 30 minutes or more;

whereby the flaky particulate material comprising substrate particles having surfaces coated with the fatty acid metal salt is provided, the fatty acid metal salt being present on the substrate particles in an amount of 0.1 to 15% by mass, the flaky particulate material having an average coefficient of friction of not more than 0.50 and a total light transmittance of not less than 85%.

2. The process according to claim 1 wherein the substrate particles are selected from particles of mica, synthetic mica, sericite, talc, barium sulfate and aluminum oxide.

3. The process according to claim 1 wherein the flaky particulate material has a reflection-intensity ratio (0°/45°) of not less than 0.30, said ratio (0°/45°) meaning a ratio: (a reflection intensity in the condition that the light incident angle is −45° and an acceptance angle is 0°)/(a reflection intensity in the condition that the light incident angle is −45° and the acceptance angle is 45°), and said ratio being measurable by a three-dimensional variable gloss meter.

4. The process according to claim 1, wherein the flaky particulate material has an average major axis length of 3 to 40 μm, and the ratio of the average major axis length to the average particle thickness of the flaky particulate material is 3 to 300.

* * * * *